(12) United States Patent
Stiles

(10) Patent No.: US 9,393,361 B2
(45) Date of Patent: *Jul. 19, 2016

(54) METHOD TO DETERMINE A MATERIAL DISTRIBUTION

(71) Applicant: Medtronic, Inc., Minneapolis, MN (US)

(72) Inventor: David Stiles, Danvers, MA (US)

(73) Assignee: Medtronic, Inc., Minneapolis, MN (US)

( * ) Notice: Subject to any disclaimer, the term of this patent is extended or adjusted under 35 U.S.C. 154(b) by 669 days.

This patent is subject to a terminal disclaimer.

(21) Appl. No.: 13/714,555

(22) Filed: Dec. 14, 2012

(65) Prior Publication Data

US 2014/0171900 A1    Jun. 19, 2014

(51) Int. Cl.
*A61M 5/14* (2006.01)
*A61M 25/00* (2006.01)
*G06F 19/00* (2011.01)
*A61M 5/142* (2006.01)

(52) U.S. Cl.
CPC .......... *A61M 5/14* (2013.01); *A61M 5/142* (2013.01); *G06F 19/3437* (2013.01); *G06F 19/3481* (2013.01); *A61M 2005/14208* (2013.01)

(58) Field of Classification Search
CPC ............ A61M 2005/14208; A61M 5/14; A61M 5/142; G06F 19/3437; G06F 19/3481
See application file for complete search history.

(56) References Cited

U.S. PATENT DOCUMENTS

| | | | |
|---|---|---|---|
| 5,740,808 A | 4/1998 | Panescu et al. | |
| 5,964,705 A | 10/1999 | Truwit et al. | |
| 5,983,126 A | 11/1999 | Wittkampf | |
| 6,026,316 A | 2/2000 | Kucharczyk et al. | |
| 6,381,485 B1 | 4/2002 | Hunter et al. | |
| 6,464,662 B1 | 10/2002 | Raghavan et al. | |
| 6,482,182 B1 | 11/2002 | Carroll et al. | |
| 6,493,573 B1 | 12/2002 | Martinelli et al. | |
| 6,516,212 B1 | 2/2003 | Bladen et al. | |
| 6,549,803 B1 | 4/2003 | Raghavan et al. | |
| 7,371,225 B2 | 5/2008 | Oldfield et al. | |
| 7,570,791 B2 | 8/2009 | Frank et al. | |
| 7,715,902 B2 | 5/2010 | Hartlep et al. | |
| 7,751,865 B2 | 7/2010 | Jascob et al. | |
| 7,835,778 B2 | 11/2010 | Foley et al. | |
| 8,112,292 B2 | 2/2012 | Simon | |

(Continued)

FOREIGN PATENT DOCUMENTS

EP    1768062 A1    3/2007
EP    07106176      4/2007

(Continued)

OTHER PUBLICATIONS

International Search Report and Written Opinion mailed Jul. 16, 2014 for PCT/US2013/073655 claiming benefit of U.S. Appl. No. 13/714,555, filed Dec. 14, 2012.

(Continued)

*Primary Examiner* — Michael Rozanski
(74) *Attorney, Agent, or Firm* — Harness, Dickey & Pierce, P.L.C.

(57) ABSTRACT

A combination material can be infused into a subject and a determination can be made of a VOD and/or a convection gradient of a liquid material portion in the VOD. The combination material can be infused in the subject using selected parameters. A correlation of data relating to the liquid material can be made to a selected material to determine parameters for infusion the selected material.

21 Claims, 3 Drawing Sheets

(56) References Cited

U.S. PATENT DOCUMENTS

| | | | |
|---|---|---|---|
| 8,295,914 B2 | 10/2012 | Kalafut et al. | |
| 9,008,752 B2* | 4/2015 | Stiles | 600/411 |
| 9,020,224 B2* | 4/2015 | Stiles et al. | 382/128 |
| 2003/0114752 A1 | 6/2003 | Henderson et al. | |
| 2005/0049486 A1 | 3/2005 | Urquhart et al. | |
| 2005/0085714 A1 | 4/2005 | Foley et al. | |
| 2005/0085720 A1 | 4/2005 | Jascob et al. | |
| 2008/0081982 A1 | 4/2008 | Simon et al. | |
| 2009/0270712 A1 | 10/2009 | Raghavan et al. | |
| 2010/0240986 A1 | 9/2010 | Stiles | |
| 2012/0209110 A1 | 8/2012 | Bankiewicz et al. | |
| 2013/0287272 A1 | 10/2013 | Lu et al. | |
| 2013/0287275 A1 | 10/2013 | Stiles et al. | |
| 2014/0171781 A1 | 6/2014 | Stiles | |

FOREIGN PATENT DOCUMENTS

| | | | |
|---|---|---|---|
| EP | 1788499 | A1 | 5/2007 |
| EP | 1980201 | A2 | 10/2008 |
| WO | WO-2011008982 | A1 | 1/2011 |
| WO | WO-2012116747 | A1 | 9/2012 |

OTHER PUBLICATIONS

International Search Report and Written Opinion for PCT/US2013/073676 mailed Jul. 16, 2014 (claiming benefit of U.S. Appl. No. 13/714,563, filed Dec. 14, 2012).

BrainLab. 2006 BrainLab AG. Printed in Germany. NS-FL-E-iPlanFLOW Rev. 2.0506 Q:2.000. (2 pages).

Cabezas, et al. "Areview of atlas-based segmentation for magnetic resonance brain images." Computer Methods and Programs in Bioomedicine. (2011) pp. e158-e177.

Documentation/4.1—SlicerWiki, http://wiki.slicer.org, (2012) p. 1-6.

Linninger, et al., "Annals of Biomedical Engineering." 2007.

Linninger, et al., "Mimic Image Reconstruction for Computer-Assisted Brain Analysis," 2005.

Linninger, et al., "Neurosurg," Focus, 2006, vol. 20.

Morrison PF, et al., "High-flow microinfusion: tissue penetration and phar-acodynamics." Am J Physiol, 1994, vol. 266, R292-R305.

Morrison PF, et al., "High-flow microinfusion: tissue penetration and phar-macodynamics."Am J Physiol, 1994, vol. 266, R292-R305.

Sampson, JH, et al. "Colocalization of gadolinium-diethylene triamine pentaacetic acid with high-molecular-weight molecules after intracerebral convection-enhanced delivery in humans." Neurosurgery, Sep. 2011; 69(3):668-76.

Synchromed II—Infusion system patient manual. (2003) pp. 1-72.

Xiaomin ,Su, et al. "Real-time MR Imaging with Gadoteridol Predicts Distribution of Transgenes After Convection-enhanced Delivery of AAV2 Vectors." The American Society of Gene & Cell Therapy.www.moleculartherapy.org., vol. 18 No. 8, 1490-1495, Aug. 2010.

* cited by examiner

METHOD TO DETERMINE A MATERIAL DISTRIBUTION

FIELD

The subject disclosure is directed to a method and apparatus for assisting in determining therapy parameters, and particularly to determining a steady state volume of a material infused into a subject based upon a selected set of parameters.

BACKGROUND

This section provides background information related to the present disclosure which is not necessarily prior art.

In providing a selected material for therapy, the selected material can be infused to achieve a therapeutic effect in a region of interest in a subject. The subject can include a human patient and the region of interest can include all of or a portion of a brain, spinal cord and other selected regions of the subject. Generally, the material being infused will affect the region of interest to achieve a selected outcome.

SUMMARY

This section provides a general summary of the disclosure, and is not a comprehensive disclosure of its full scope or all of its features.

A selected material (also referred to as a therapy material) can be infused into a subject to provide a therapy to the subject. The selected material will generally have a therapeutic effect at a certain concentration in the subject. The physical region or three-dimensional volume where the concentration is at the level that elicits the desired or selected therapy in the subject is generally termed the volume of efficacy (VOE). The material can be infused into the subject into a region that is a three-dimensional volume generally termed the volume of distribution (VOD) which includes the entire three dimensional volume that is contacted by the selected material. The VOE is generally within the VOD and is based on a concentration gradient of the infused material within the VOD. The amount of material infused into the subject is generally termed the volume of infusion (VOI). The VOI may not be the same as either the VOD or VOE due to removal, such as clearance, of the selected material from the region into which it is infused.

The selected material is generally infused into a region of interest (ROI) which can include a region of interest of therapy (ROIT). The ROIT can include portions of a subject, such as spinal cord or brain, including a putamin, a caudate, and other selected regions. Generally, a catheter can be provided to or near the selected ROIT to infuse the selected material to the ROIT.

Determining the VOE within the subject can be based upon determining VOD of an infusate into a subject using various techniques. For example, a combination material that includes a selected material for a therapy and a liquid can be infused into a subject and a determination can be made based upon the VOD or a concentration gradient of the infused material in the VOD. The VOD and concentration gradient of the liquid material can be used to predict a VOD and VOE of the selected material within the subject. The combination material can be infused in the subject using selected parameters, as discussed herein, and the subject can then be analyzed to determine a VOD and a concentration gradient of the liquid to determine a VOE of the selected material for the therapy based upon the selected parameters. The VOD and concentration gradient of the liquid can be determined with T2-weighted Magnetic Resonance Image data. The VOD and concentration gradient of the selected material can be based on various studies, such as post infusion analysis of tissue samples.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
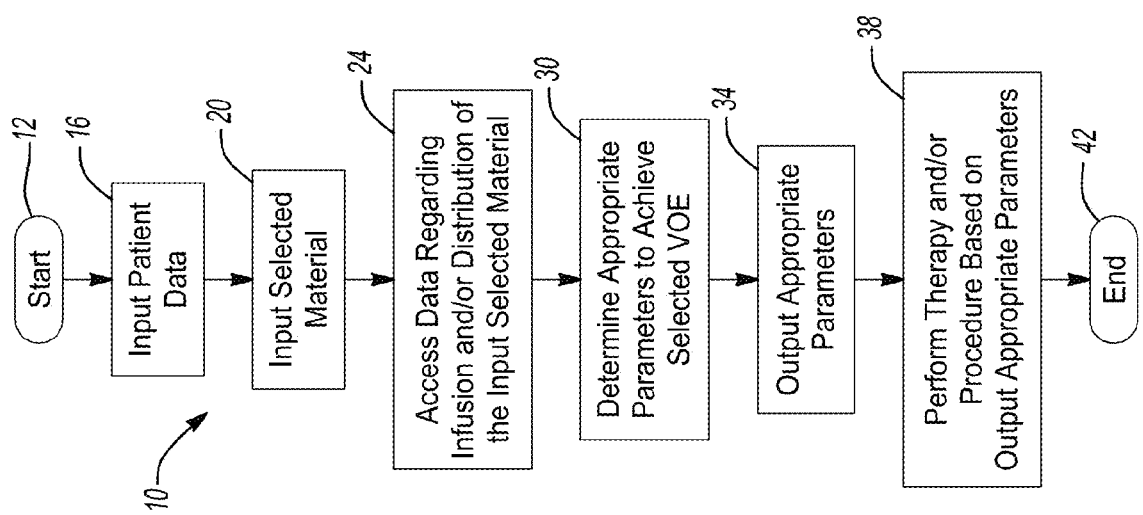
FIG. 1 is a flowchart of a method of determining parameters to generate a selected volume of efficacy in a subject.

According to various embodiments, a method of performing a therapy on a selected subject is illustrated in FIG. 1. A flowchart 10 illustrates a method of performing a therapy on a selected subject using a selected material, the selected material can be a therapy material for performing the therapy. For example, selected materials can include a small inhibiting ribonucleic acid (siRNA), steroids, or other selected materials. The selected materials can include naturally occurring materials, concentrated naturally occurring materials, or synthetic materials. Nevertheless, the selected material can generally be understood to be a drug or pharmaceutical that can be infused into a selected subject, such as a human patient, to provide a therapy to the human patient. The infusion of the selected material can be into selected anatomical regions such as a brain, spinal cord, or other tissue regions. Generally, the method of flowchart 10 allows for the determination of an infusion parameter or set of parameters for achieving a selected therapy in a patient. Moreover, it is understood that the patient data and related parameters can be for infusion into any appropriate subject whether or not an animal subject.

According to various embodiments, the method in flowchart 10 can begin in start block 12. The procedure that can proceed to inputting patient data in block 16. Inputting patient data can be inputting selected data regarding the patient, including a disease to be treated, and other patient data. For example, patient data can include image data of the patient, such as image data of a brain. Image data of a brain can include MRI or computed tomography (CT) images. In the image data of the patient, a selected region can be determined, as discussed above including a region of interest for therapy (ROIT). The ROIT can be the area (including a volume in the region) in which a volume of efficacy (VOE) is selected to be achieved. The VOE can be a three dimensional volume within the brain or any selected anatomical region, where the concentration of the selected material is appropriate to achieve a desired or selected result in treating the patient. For example, a VOE of a siRNA can be the volume in which the concentration of the siRNA is high enough to achieve inhibition of a selected gene or expression of a gene. Accordingly, input patient data in block 16 can include the determination or selection of an ROIT in an area in which the VOE should be achieved.

Additional patient data input in block 16 can include weighting patient data, inputting patient-specific data including age, alternative or additional diagnoses and other selected information. Weighting the patient data can include weighting image data of the patient to identify the ROIT, regions to not be contacted by the selected material, boundaries or anatomical regions, etc. It is understood, however, that the input patient data in block 16 can include any appropriate data to assist in determining and treating the patient.

Inputting of selected material in block 20 can be inputting the selected material for providing the therapy to the patient. It is understood that inputting the selected material can also be done when inputting the patient data in block 16, but is separated here for clarity of the current discussion. The selected material can be the material that is selected for providing a therapy to the patient and based upon which the VOE can be based. The selected material can be any appropriate material, as noted above, and can include a drug to treat the identified disease of the patient.

Figure 4:
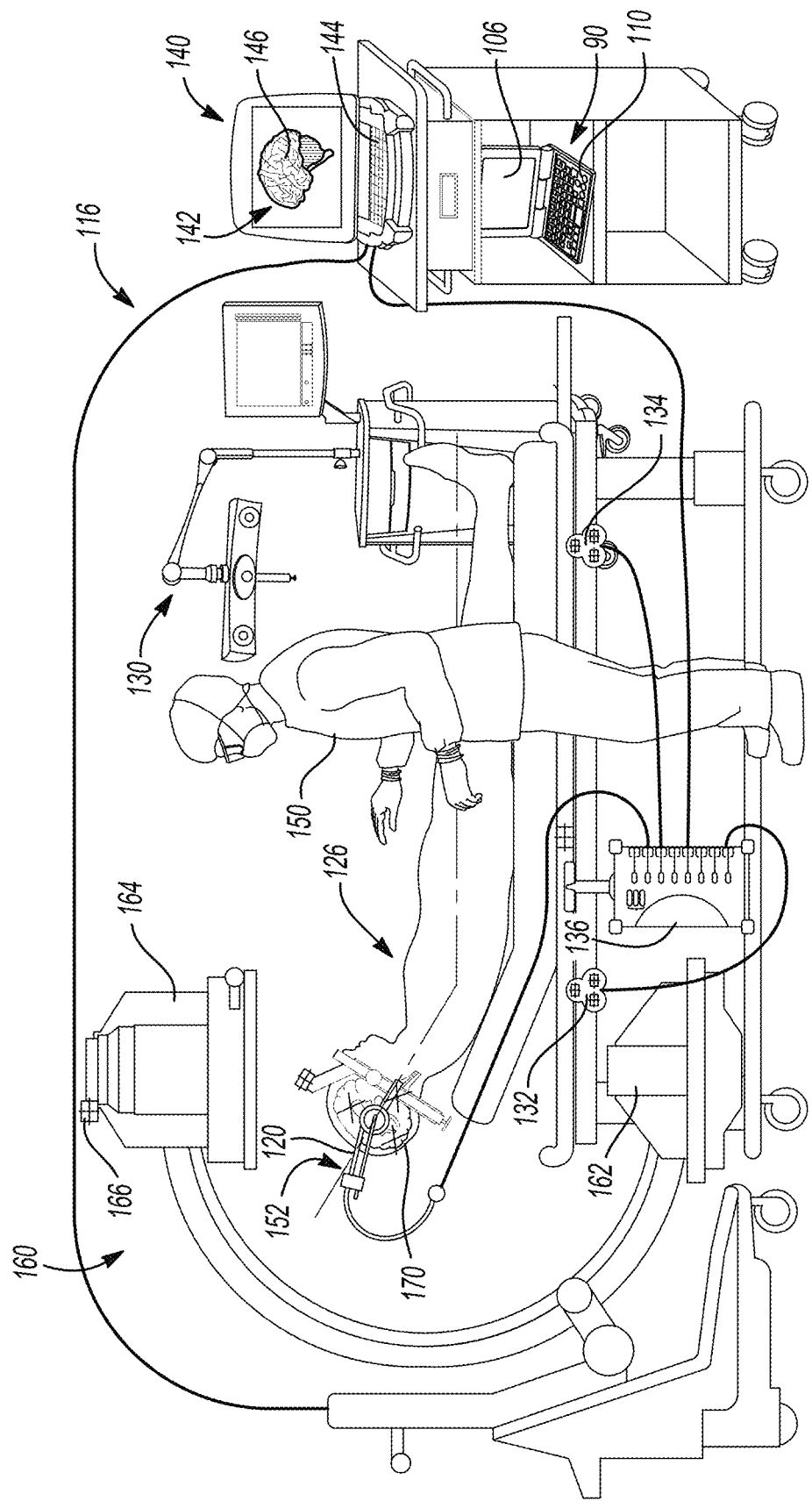
FIG. 4 is a schematic and environmental view of a therapy system.

The selected material input in block 20 can then be used to access data regarding infusion and/or distribution of the input selected material in block 24. That is, accessing data regarding infusion of the selected material can be based upon the selected material input from block 20. Accessing the data in block 24 can be any appropriate accessing, such as accessing a stored database of infusion data regarding a selected material or a plurality of selected materials, inputting infusion parameters of the selected material input in block 20, or other appropriate accessing. For example, as illustrated in FIG. 4, a processor system 90, 140 that can include a processor that is able to access a memory system that has stored in it a database of infusion data. The processor can execute an algorithm to access the data and perform the other steps of the method 10. The data accessed in block 24 can be appropriate data regarding the infusion which can include distribution of the material into a subject, such as into the brain of a human subject, which will be discussed in further detail herein.

The access data regarding infusion of the input selected material in block 24 and the patient data in block 16 can be used to determine parameters to achieve a selected VOE in block 30. Determining appropriate parameters for achieving a selected VOE block 30 can be performed according to various processes. For example, a computer algorithm can be executed as a plurality of instructions by a processor of the processor system 90, 140 to determine a selected VOE and the parameters to achieve the selected VOE. The determination of parameters to achieve the selected VOE can also be based upon other factors, such as the volume of distribution (VOD), the volume of infusion (i.e. the amount of material infused in the subject), the position of the VOD and VOE relative to other structures in the patient, and other selected factors. In addition, the executable instructions can include determining volumes of greater or lesser convection (e.g. flow of material due to pump forces through a source catheter or channel) to determine the volume and timing for achieving a selected VOE. Exemplary systems to determine the parameters for a selected VOE are disclosed in concurrently filed U.S. patent application Ser. No. 13/714,550 incorporated herein by reference. The system, briefly, can analyze the input patient data from block 16, the input selected material from block 20, and the accessed data regarding the input selected material in block 24 to determine at least a VOE and/or a VOD of the selected material in the patient. The accessed data can also include determinations of convection enhanced delivery and diffusion delivery of the material. The data can be provided through T2 weighted MRI image data of the patient or previously acquired T2 weighted MRI image data from subject models. Various weights and costs factors can then be used to determine a cost of one or more determined VOD and/or VOE in the selected subject. Accordingly, the system can search for or determine, based upon selected parameters and instructions, parameters to achieve the selected VOE in the selected subject that has a lowest cost or cost within a range or threshold.

Once an appropriate set of parameters have been determined in block 30, the parameters can be output in block 34. The parameters can be output in any appropriate manner, such as outputting them as a visual display on a display device (e.g. 106, 142 in FIG. 4), as discussed further herein, for viewing by a user (150 in FIG. 4). Additionally, the output can include a hard copy output, such as a print-out output for assisting in performing and preparing for a therapy. Additionally, it is understood that the parameters can be transferred to a device to provide a therapy to a subject, such as a pump that can pump the selected material to the patient through a catheter (e.g. catheter 120 in FIG. 4).

The parameters can include any appropriate parameters for performing a therapy on a patient. Certain parameters can include infusion parameters that can include a location of an infusion site in the subject. The location of the infusion site can be the specific three dimensional location of an open port of an the infusion catheter 120 within the subject 126. Additionally, the infusion parameters can include the type and/or number of infusion catheters that can be positioned at one or more sites in the subject. The type of infusion catheter can include single port, porous infusion catheters, or multiple port infusion catheters. Additional parameters can include flow rates (including high flow rates and low flow rates) and time at flow rates (including times at high flow rates and times at low flow rates). The infusion parameters can also include the concentration of the selected material for infusion into the patient.

Once the infusion parameters are output in block 34, a therapy can be performed on the patient in block 38. Performing the therapy on the patient can include positioning the infusion catheter in the patient for delivering the selected material to the patient, as illustrated in FIG. 4 and described in further detail below. The catheter can be positioned in the patient using appropriate systems, such as tracking and computer assisted navigation systems for positioning the catheter at the selected location based upon the parameters output in block 34. Appropriate navigation systems can include The StealthStation® surgical navigation systems (including electromagnetic and optical tracking systems), sold by Medtronic, Inc. and those disclosed in concurrently filed U.S. patent application Publication Ser. No. 13/714,550, all of which are incorporated herein by reference. Performing the therapy can then include delivering or infusing the selected material into the patient such as with a pump or other delivery device. It is understood that performing the therapy can include implanting a pump into a patient for a chronic delivery or delivering the material over relatively short period of time for an acute delivery of the therapy. The pump can provide convection forces to the flow of the material into the patient.

Once the therapy is completed, either for an acute therapy or a system initially positioned (e.g. including implantation of a pump and positioning of a infusion catheter), the method can end in block 42. The ending of the method can include completing a procedure to position the catheter and pump and delivering an initial dose of therapy, such as in an acute therapy. It is understood that the delivery of a material can include an infusion into the subject and infusion parameters can be used in determining appropriate parameters for achieving a therapy. Convection enhanced diffusion (CED) can be one method of delivering the material for infusion into the subject and can include the infusion, such as with a pump, of a material into the subject.

Figure 2:
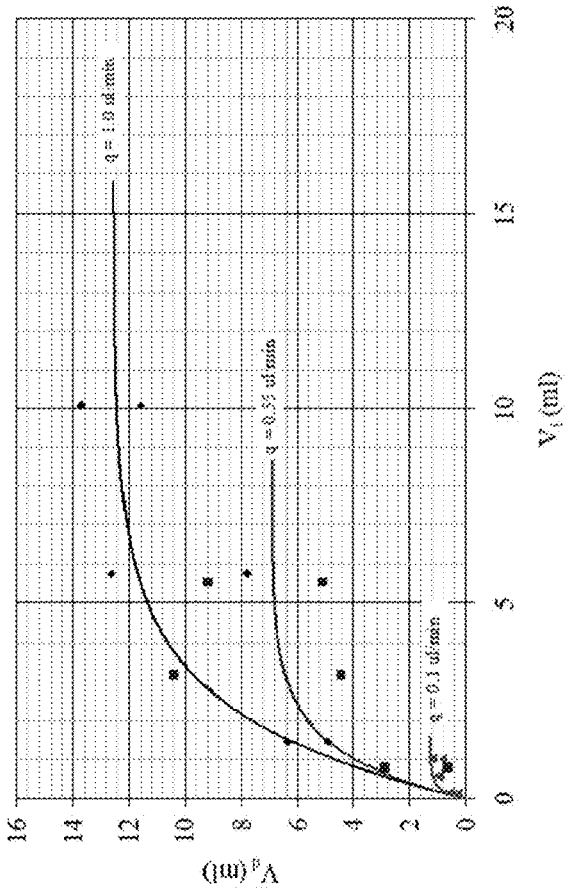
FIG. 2 is a graph of steady state volumes of distribution at differing flow rates.
Figure 3A:
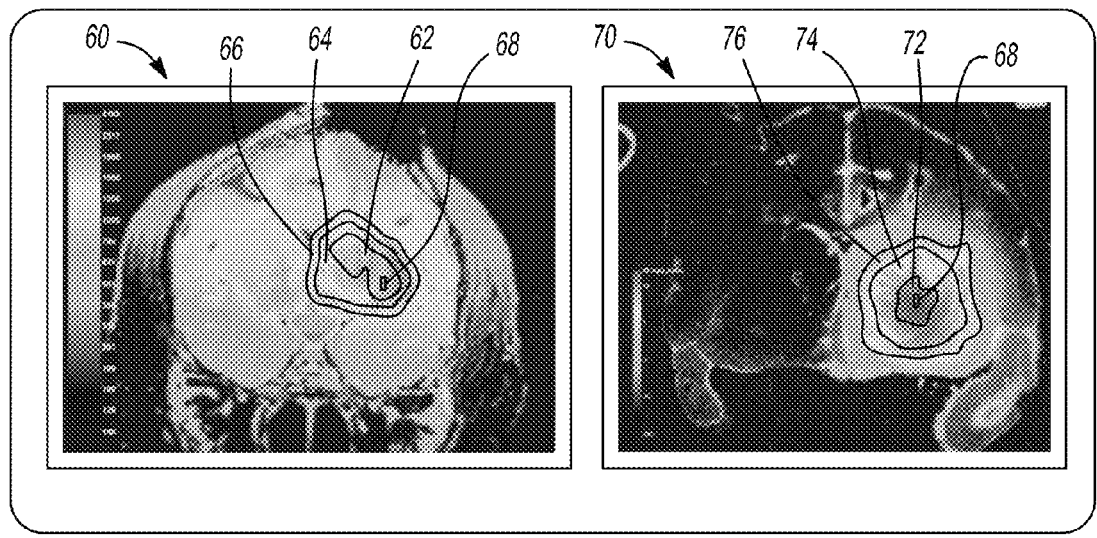
FIG. 3A illustrates a first screen shot and a second screen shot illustrating two volumes of distribution.
Figure 3B:
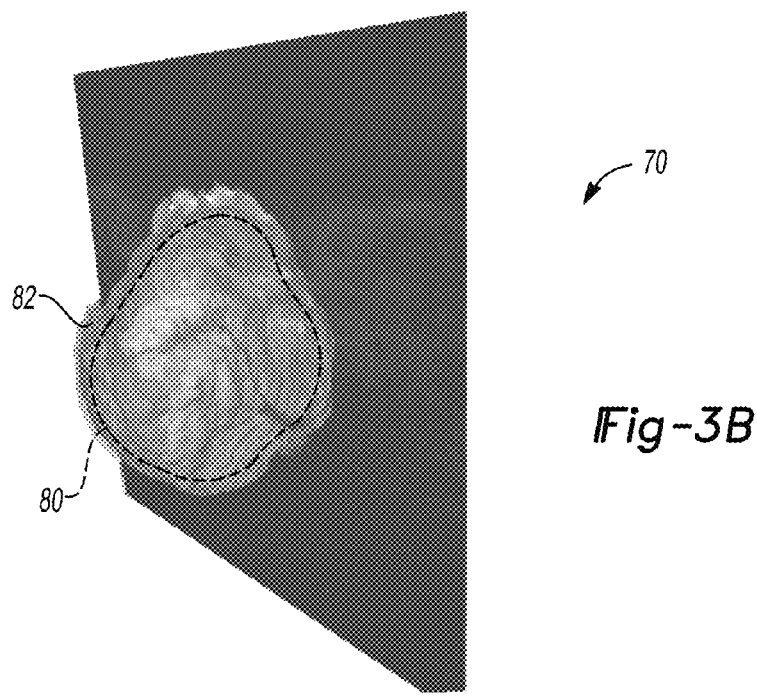
FIG. 3B illustrates a screen shot illustrating two volumes of distribution.

With continuing reference to FIG. 1 and additional reference to FIGS. 2, 3A, and 3B, the accessed data from block 24 can be data that is accessed regarding the selected material. The data that is accessed regarding the selected material can include information relating to the physical flow of the selected material into the patient. The accessed data can also include data regarding interaction of the selected material with the subject, such as pharmacodynamic (PD) and pharmacokinetic (PK) information. Additionally, or as an alternative thereto, information can be determined and stored regarding a flow of a material into a subject. For example, flow of a material can be analyzed to determine a steady-state volume of distribution (SSVOD) of the material in a subject. The SSVOD is a VOD that is reached based on a single set of infusion parameters. The SSVOD can be based upon selected infusion parameters, including those discussed above.

The SSVOD can be based on the single set of infusion of parameters which can generally yield a single SSVOD after a period of time. The SSVOD can be determined based upon analysis or experimentation on the subject. The SSVOD can, however, also vary over time if the infusion parameters vary over time. The SSVOD of the infused material, once achieved, includes a concentration gradient from the point of infusion into the patient to the outer boundary of the SSVOD. The concentration gradient can be used to determine the VOD and the VOE, generally within the VOD, of the selected material into the subject. It is further understood, that the analysis can occur at any appropriate time after infusion has begun. Thus, the SSVOD need not be reached to acquire study data including T2 weighted MRI image data and selected material concentration gradient data.

The selected material to be infused into the subject, however, can generally be a therapeutic material which can have both beneficial and inhibitive actions on a patient. For example, a pharmaceutical drug that is infused into a patient as the selected material may have beneficial therapies and effects on a patient at a selected concentration and in a selected location, but can have a negative impact on a patient if in a different concentration and/or at a different location. Additionally, certain locations where the material is administered are more efficacious than other locations. For example, infusing the selected material into a sulcus may not be very efficacious for the patient. The sulcus or blood pathways can greatly decrease the VOE of the selected material on the patient and causes unselected clearing of the selected material from the patient without allowing time for the selected material to affect the patient.

To assist in determining the VOD and a concentration gradient within the VOD, a study of the material after infusion into a subject or a model of the subject (e.g. a subject model can include an animal model, such as rhesus monkeys (Macaca mulatta)) can be performed. The study can include an imaging study, such as specific magnetic resonance imaging (MRI) study. The imaging study can include a T2 weighted MRI (T2-MRI or T2). Information determined from the infusion imaging study can be used to determine a VOD and a concentration gradient within the subject for which the data is input in block 16. During a study period, the selected material can be injected or infused into a patient or subject model at selected study infusion parameters (such as those infusion parameters discussed above), to generate, during a test or study period, a database or table of VOD and concentration gradients of the material at the study infusion parameters. The material information can be obtained by infusing subject models with the selected material and then imaging the subject model to identify a study VOD and a study concentration gradient within the VOD of the material.

To assist in determining the VOD and a concentration within the VOD, a study of the selected material infused into a subject or a model of the subject (i.e. a subject model) can be performed. A study VOD and a study concentration gradient can be determined using an imaging modality to image the subject or subject model. For example, T2-weighted MRI data can illustrate the location of liquids in image data. T2 weighted MRI images can include or be generated of a subject or subject model to view and analyze the location of the liquid in the subject or subject model. As the material that is infused into the subject or subject model is generally in a liquid form, the T2 weighted MRI can be used to determine the location of the infused material. For example, the infused material can be injected into the patient and then the patient is imaged using the T2 weighted MRI image data.

The T2 weighted MRI image data generally illustrates and allows for determination of movement of a liquid (e.g. water included with or of the selected material) within the subject or subject model. In other terms, the T2 weighted MRI image data can be used to determine or illustrate one or more regions of convection. The T2 weighted MRI, thus, illustrates convection or high convection regions within the image data. The high convection region and/or regions can correlate to the high T2 weighted MRI signal in the image data. In addition, various levels of convection can be determined and imaged in the T2 weighted MRI. Thus, varying convection levels can also be determined. Thus, T2 weighted MRI image data of the subject and/or subject model can be used to illustrate those regions where high convection and/or varying levels of convection are occurring. The varying levels of convection can be imaged and determined as a convection gradient within the test subject. The convection gradient, including regions of the high convection, can be used by the modeling systems, including the executable instructions discussed above, to determine and/or illustrate the VOE.

The T2 weighted MRI image data can be compared to other analyses of the subject or subject model. Other analyses can include a post-mortem analysis of a concentration and related volumes of the concentration of the selected material that is infused into the subject model. For example, the subject model can be infused with the selected material at selected infusion parameters and the subject model can be imaged with a T2 weighted MRI. The subject model can then be analyzed post-mortem to determine concentration of the selected material within the tissue. A radioactive isotope (e.g. radio tag) can be added to the selected material to assist in viewing or determining the concentration of the selected material within the tissue during the post-mortem analysis. Analyzing tissue with a radio tag in the selected material is generally known in the art, such as that disclosed in Stiles, David K. et al., "Widespread suppression of huntingtin with convection-enhanced delivery of siRNA", *Exp Neurol*, Nov. 19, 2012, 463-471.

The accessed data regarding the infusion and/or distribution of the selected material from block 24 can be based on a comparison of data related to infusion of the selected material into the subject or subject model. The following discussion will discuss the subject model infusion during a study period as it relates to a subject during a therapy period. The subject model can include the animal model, which is different from a subject where the subject can be a human subject. It is understood, however, that the subject model can simply be any subject that is not the subject that is to receive the therapy. Nevertheless, the information acquired during the study period can be used for a comparison and the data that is accessed in block 24.

As illustrated in FIG. 2, various flow rates (q) can be used to study the infusion of the selected materials into the subject or subject model. The flow rate can be varied and used to study the VOD ($V_d$) at various flow rates, as illustrated in FIG. 2. As further illustrated in FIG. 2, the VOD increases over time until the steady-state volume of distribution (SSVOD) is achieved. The SSVOD is achieved substantially when the curve is substantially flat and remains substantially unchanged over a selected period of time. The selected period of time to achieve the steady state can include a time that is greater than about five days, including greater than about seven days, and further including greater than about ten days or any appropriate time. The amount of change or variation that is understood to be the SSVOD can include about plus or minus 0 to 10 percent (0%-10%), including about 0%-5%, and further including about 0%-2%. The SSVOD for a chronic or long-term infusion can be determined or achieved over an extended period of time. It is understood, however, that an acute therapy can include a relatively short period of time for an infusion and that the SSVOD, where the VOD remains substantially unchanged over time, may not be achieved.

Further, as illustrated in FIG. 2, various flow rates can lead to various and different SSVODs. Thus, the SSVOD can correlate to the flow rate, again as illustrated in FIG. 2. Flow rate can be one of the parameters used to determine in selecting a therapy for a subject. Accordingly, the flow rate can be used to determine a SSVOD within the subject for determining an appropriate parameter.

The information obtained in block 24 can be based upon imaging of a subject model during a study period alone or in combination with the concentration analysis information. The information accessed in block 24 can be used during a therapy and compared to image data of the subject during or immediately subsequent to a therapy. In particular, the T2 weighted MRI can be used to illustrate the presence and/or regions of convection of a liquid. The presence and/or regions of convection of a liquid can be used to determine the presence and/or regions of convection of the selected material during an infusion therapy into the subject. The regions of convection can be discretized to determine a convection gradient to show varying levels of convection as well, as discussed and illustrated herein.

The T2 weighted MRI, however, may not directly image the selected material, but can be used to generate images to illustrate the position of a liquid within the subject and/or regions within the subject where convection is greatest. Accordingly, the study can be used to determine the position of the selected material relative to the liquid and regions of convection illustrated in the T2 weighted MRI data to determine the SSVOD of the selected material. In various examples, the selected material can be a pharmaceutical material and/or a biological material (e.g., siRNA) that is positioned in a carrier liquid for infusion. Thus, the liquid in the T2 weighted MRI image data can be liquid of the infusion. In this example, the infused material can be a combination material. The combination material can include a combination of the carrier liquid and the selected material. Where the selected material is providing the therapy to the subject.

As illustrated in FIGS. 3A and 3B, the position of the liquid in a T2 weighted MRI can be illustrated in an image generated or rendered from image data and can be displayed on a screen or display device 106, 142 (FIG. 4). A T2 weighted MRI image 60 can illustrate the position and regions of convection of the liquid using various techniques, such as a false color or gray scale differentiation of concentrations. The T2 weighted MRI image data can illustrate regions having varying Peclet numbers. The Peclet number is generally the ratio of convection flow over diffusion flow. More specifically, it is the product of velocity of a flow times a selected length divided by a coefficient of diffusion. Thus, a high Peclet number will represent a region where high convection relative to diffusion is occurring.

The regions of convection can also be illustrated as a convection gradient having selected Peclet numbers. A first convection region 62 can have a high convection, a second convection region 64 can have a medium convection, and a third convection region 66 can have a low convection. The convection gradient illustrated as regions of convection 62-66 can be illustrated relative to an icon 68 or image of a portion of a catheter to show a convection gradient within the VOD relative to the infusion site.

The different regions of convection can be predetermined or can be determined based on the determined Peclet numbers within the T2 weighted MRI image data. The numbers determined after imaging can be automatically (e.g. with a processor executing instructions) or manually selected. For example, a range of numbers or percentage can be selected for inclusion in each region. Generally a medium convection region will have a Peclet number of about 1. A high convection region will have a Peclet number greater than 1 including about 100 or greater. A low convection region will have a Peclet number less than one including about 0.01 or lower. Generally, the Peclet number is used to help determine whether convection or diffusion is more dominate in a region. Thus, a difference between a high, medium, and low region will differ by at least one order of magnitude. It is understood, therefore, that differences can include two, or three, or more orders of magnitude difference.

The convection gradient can be related to a concentration gradient that is determined from the subject model study. That is a region with high convection can be determined to have a high concentration based on the imaged convection. This can be data that is accessed in block 24 for use in executing the instructions discussed above to determine the VOE. This T2 weighted MRI image data can be acquired with an imaging system of the subject model during a study period and can relate to specific infusion parameters. Thus, a correlation can be determined to a VOD and a concentration gradient of the selected material that can be accessed in block 24 for planning and/or during a therapy.

A second screen display 70, illustrated in FIG. 3A, can include a post-mortem analysis of a subject model after infusion for a selected period, such as about seven days. The post-mortem analysis can include a radiation analysis due to the selected material being radio tagged. The image 60 and the image 70 can be acquired after the same or substantially same period of infusion. For example, image data can be taken with a T2 weighted MRI about 5 minutes to about 30 minutes prior to acquiring the tissue sample that is in the image 70. Thus, the concentration in the post mortem analysis can be related to the imaged convection in the T2 weighted MRI image data.

In the image 70, the VOD of the selected material and a concentration gradient of the selected material can be analyzed. In particular, the image 70 is based directly on the position and concentration of the selected material directly. The display 70, based on the post-mortem analysis, can also include an illustration or display of the infusion site 68 and further include an illustration of regions of a high concentration 72, a medium concentration 74, and a low concentration 76. The second screen display 70 includes a concentration gradient and VOD based upon an analysis of the actual position of the selected material due to radio tagging the selected material.

The image data in the first screen display 60 can be compared to the image data and the second screen display 70 to determine an actual distribution and concentration gradient of the selected material relative to the T2 weighted image data that illustrates the location (e.g. VOD) and regions of convection of the liquid relative to the infusion site. The comparison can be used to determine a correlation between the liquid and the selected material as the two images are taken at substantially the same time. The comparison can be used to analyze or model the VOD and concentration gradient of the selected material based upon the VOD and concentration gradient of the liquid from the infusion site 68. It will be understood that a plurality of studies and infusion parameters can be made to determine a comprehensive correlation between the location and regions of convection of the liquid in the T2 weighted MRI and the VOD and concentration gradient of the selected material based upon a post-mortem or other analysis.

With reference to FIG. 3B, the display device can display the comparison on a single display, such as an overlap three-dimensional display 78. The three-dimensional overlap display 78 can be used to illustrate the position of the selected material such as a selected material VOD 80 in comparison to a liquid VOD and/or region of convection 82. Again, the liquid VOD can be displayed based upon T2 weighted MRI data of the subject or subject model. The VOD of the selected material 80 can be based upon a correlation between the VOD and concentration of liquid due to the accessed data in block 24 and/or other analysis, such as the post mortem analysis.

Additionally, it is understood that the VOD of the liquid need not or may not be larger than the VOD of the selected material, although the illustration in FIG. 3B illustrates such. It is understood that selected materials may diffuse differently in the subject based upon the selected material relative to the liquid carrier, the anatomy or tissue of the subject, and other issues. Accordingly, it is understood that the distribution illustrated in FIG. 3B is merely exemplary and for illustration purposes of this discussion.

The correlation of the VOD and concentration gradients of the liquid based upon the T2 weighted MRI data to the location (e.g. VOD) and regions of convection of the selected material can be used to determine and assist in defining a location for an infusion and infusion parameters in a subject. Again, the subject model can be used during a study period to determine an appropriate infusion parameter and infusion location for a subject. Thus, the correlation can be used to plan a therapy for the subject.

The correlation or comparison between the location (e.g. VOD) and regions of convection of the liquid from the T2 weighted MRI and the VOD of the selected material can be saved as a comparison database or comparison factor. The stored comparison can be used for determining or predicting a VOD and/or concentration gradient of the selected material based upon the location (e.g. VOD) and regions of convection of the liquid determined in the T2 weighted MRI data. The database or factor can be stored in a memory system, such as a memory system of the systems 90, 94 illustrated in FIG. 4 that are accessed in block 24 of FIG. 1. The correlation factor or database is used to predict variations of the VOD of the liquid and the VOD of the selected material that can be based upon various parameters and differences. Accordingly, the database can be used to analyze infusion parameters for a selected subject.

Infusion parameters that are determined or used during the study can include concentration of the selected material relative to a carrier liquid, an infusion location (i.e., catheter location), a catheter type, a number of catheters and their relative locations, high and low flow rates, and times at high/low flow rates. Each of these parameters can be analyzed during the study period to determine a location (e.g. VOD) and regions of convection of the liquid in the T2 weighted MRI image relative to the determined VOD and concentration gradient of the selected material in the subject model. Once the study has been used to determine the correlation of the liquid location (e.g. VOD) and regions of convection in the T2 weighted MRI data relative to the VOD and concentration gradient of the selected material, the correlation can be used to determine appropriate parameters to achieve a selected VOD in block 34 and output the appropriate parameters in block 34.

The correlation can allow a user 150 (FIG. 4), such as a surgeon, to infuse the selected material into the subject and image the subject to determine the location (e.g. VOD) and regions of convection of the liquid based on T2-weighted MRI data. Based on the location (e.g. VOD) and regions of convection in the T2-weighted MRI data a determination of the VOD and concentration gradient of the selected material can be made and/or predicted. Accordingly, a post-mortem analysis need not be required of the subject to determine an actual or predicted concentration gradient and VOD of the selected material. Additionally, a contrast agent need not be infused with the selected material and/or the carrier liquid to determine a VOD and concentration gradient of the infusion material in imaging data. The T2 weighted MRI data can be used to determine the location (e.g. VOD) and regions of convection of the liquid and the correlation accessed in block 24 can be used to determine the VOD and concentration gradient of the selected material. Thus, the subject can be infused with the selected material, which can be the combination material, and the subject in the be imaged with the T2 weighted MRI imaging technique to determine a location (e.g. VOD) and regions of convection of the liquid and the information accessed in block 24 can be used to determine the VOD and concentration gradient of the selected material.

According to various embodiments, once a selected infusion has occurred and the subject has been imaged, the image data and image can be displayed, as illustrated in FIG. 3B, to illustrate a VOD and/or concentration gradient to the liquid 82 relative to a determined or predicted VOD and concentration gradient of the selected material 80. It is understood, however, that the illustration can simply be icons generated for viewing by the user 150. Additionally, an icon can include the icon 80 that is superimposed on the actual image data of the location (e.g. VOD) and regions of convection of the region into which the infusion has occurred with the selected material for viewing by the user 150. Regardless, it is understood that the VOD and concentration gradients of the liquid and the selected material need not be overlayed on one another for viewing by the user 150. Nevertheless, the user can analyze the relative VODs and concentration gradients of the liquid and the selected material to determine the therapy. Additionally, a planning system 90, as discussed further herein, can be used to plan and control infusion into the subject based upon the accessed data in block 24 and the image data of the subject to determine appropriate infusion parameters or altering infusion parameters.

To plan and perform the therapy, with reference to FIG. 4, a planning system can include a planning processor system 90 that can access a memory system than includes the database from block 24 and execute instructions at least for determining the appropriate parameters in block 30, discussed further herein. Briefly, however, the accessed database 24 can include data regarding VOD and/or VOE of the selected material based on infusion parameters and related to the location (e.g. VOD) and/or regions of convection of the liquid. The processor system 90 can use the accessed data from block 24 to determine a predicted VOD and/or VOE of the selected material within a subject based at least on the accessed data including selected material information and infusion parameter information. The planning processor system 90 can include a display device 106 to display the output parameters from block 34. An input device 110 can include a keyboard or other input devices, including a touch-screen or computer input mouse device, to allow for a user to input various parameters and information, including the input patient data from block 16 and the input selected material from block 20.

As further illustrated in FIG. 4, a navigation system 116 can navigate and/or guide the selected catheter 120 into the patient 126 for performing a procedure and applying the therapy in block 38. As discussed above, and incorporated herein by reference, a navigation system is disclosed and described in U.S. patent application Ser. No. 13/714,550 is appropriate and is incorporated herein by reference. Generally, the navigation system 116 can include one or more navigation systems including an optical navigation system having an optical localizer 130 and/or an electromagnetic navigation system including one or more electromagnetic localizers 132 and 134. The electromagnetic localizers 132, 134 can communicate with a localizer array and probe interface 136.

The array controller and probe interface 136, alternatively or in combination with the optical localizer 130, can communicate with a navigation processor system 140. The navigation processor system 140 can include a display device 142 and an input device 144. The display device 142 can display image data 146, such as image data of the patient 126 including that inputted in block 16. The display device 142 can also display image data of the patient 126 that is the T2-weighted MRI image data for determination of the location (e.g. VOD) and regions of convection of the liquid in the patient 126.

The planning processor system 90 and/or the navigation processor system 140 can be operated or used by the user 150 to plan for and/or perform a procedure and therapy on the patient 126, such as performing the therapy in block 38. As discussed above, the instrument 120 can include a catheter that is positioned within the patient 126. The instrument 120 can be passed through an instrument guide 152 into the subject 126. The guide 152 can be navigated with the navigation system 116 that tracks with either the electromagnetic tracking system or the optical tracking localizer 130.

Additionally, image data can be acquired of the patient 126 such as with a x-ray imaging system 160 that can include an x-ray emission section 162 and an x-ray receiving section 164. The imaging system 160 can be tracked with an imaging system tracking device 166. It is understood that the imaging system 160 can also include other appropriate imaging systems, such as a magnetic resonant imaging (MRI) system, computed tomography (CT), or other appropriate imaging system. The MRI imaging system can be used to acquire T2-weighted MRI data. Regardless, the instrument 120 can be guided and navigated into a brain 170 of the patient 126 for performing the therapy on the patient 126. It is understood that the patient 126 can be registered to the image data for performing a procedure, as is generally understood in the art. Icons can then be displayed on the display device 142 to illustrate the position of the catheter or the instrument 120 relative to the image data 146 displayed on the display device 142.

Additionally, the location (e.g. VOD) and regions of convection of the liquid can be displayed on the display devices 142 and/or 106. Also, the VOD and concentration gradient of the selected material, based on the correlation factor discussed above, can be illustrated on the display devices 142 and/or 106. As discussed above, they can be shown separately or superimposed on one another and/or illustrated relative to the image data 146. It is understood that the VOD and regions of convection and/or the concentration gradient of both the liquid and the selected material can be displayed as icons on the display device 106, 142 as illustrated in FIGS. 3A, 3B, and 4 to illustrate the location of the respective VODs and concentration gradients. Also, they can be displayed relative to the ROIT or other selected regions of the subject. Accordingly, it is understood that a therapy can be planned, such as determining an appropriate set of parameters to achieve a selected VOE, on the planning processor system 90 and a procedure can be performed, such as being able to provide therapy to the subject 126, either directly or using the navigation system 116. Regardless, the data accessed in block 24 can be used to assist in determining the VOD, concentration gradient in the VOD, and/or the VOE of the selected material from block 20 in the selected patient.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of determining a selected set of parameters for a therapy on a subject, comprising:
   selecting a material to provide to the subject for the therapy;
   accessing a database of predetermined distribution data related to the selected material, wherein the predetermined distribution data is determined prior to the therapy on the subject;

executing instructions with a processor to determine at least one infusion parameter to achieve a selected volume of efficacy in the subject of the selected material; and outputting the determined at least one infusion parameter for the therapy on the subject;

wherein the database is based on analyzing T2 weighted magnetic resonance image data of a subject model after having infused in the subject model the selected material as a combination material including the selected material at study infusion parameters;

wherein executing instructions with a processor to determine at least one infusion parameter is based on analyzing a Peclet number of image data of the subject after infusing the selected material into the subject and the predetermined distribution data.

2. The method of claim 1, further comprising:
infusing the combination material including the selected material into the subject model to a steady state distribution with a study set of parameters.

3. The method of claim 2, further comprising:
imaging the subject model with the selected material at a selected time during or after infusion of the combination material in the subject model;
determining a study volume of distribution of the selected material at the selected time; and
determining a concentration gradient of the selected material within the study volume of distribution within the image data.

4. The method of claim 3, wherein determining the study volume of distribution of the selected material at the steady state further includes evaluating a distribution of the selected material within a tissue of the subject model;
wherein determining a concentration gradient of the selected material within the study volume of distribution within the image data further includes evaluating a concentration gradient of the selected material within a tissue of the subject model within the evaluated distribution.

5. The method of claim 4, wherein evaluating the distribution of the selected material within a tissue of the subject model includes:
obtaining a tissue sample of the subject model; and
determining a concentration gradient of the selected material within the tissue sample.

6. The method of claim 4, further comprising:
correlating the volume of distribution of a liquid material of the combination material in the image data to a volume of distribution of the selected material.

7. The method of claim 6, wherein correlating the volume of distribution of the liquid material to the volume of distribution of the selected material further includes:
infusing the combination material including the liquid material and the selected material into the subject model; and
comparing the liquid volume of distribution and a related liquid convection gradient to the volume of distribution of the selected material and a related selected material concentration gradient within the subject model.

8. The method of claim 7,
wherein infusing the combination material into the subject model is with a first set of infusion parameters to achieve a steady state volume of distribution in the subject model;
wherein executing instructions with the processor to determine at least one infusion parameter to achieve the selected volume of efficacy in the subject of the selected material includes evaluating the steady state liquid volume of distribution in the subject model to determine a related selected material volume of distribution at a steady state within the subject.

9. The method of claim 8, wherein executing instructions with the processor to determine at least one infusion parameter to achieve the selected volume of efficacy in the subject of the selected material further includes relating the first set of infusion parameters to a second set of infusion parameters for the selected material to achieve the selected volume of efficacy of the selected material within the subject.

10. The method of claim 9, further comprising:
displaying the volume of efficacy as an icon superimposed on an image of the subject.

11. A method of determining a selected set of parameters for a therapy on a subject, comprising:
accessing a database of predetermined correlations of parameters relating a liquid material of a combination material to a selected material, wherein the combination material includes the liquid material and the selected material;
analyzing a Peclet number from image data of the subject after having infused in the subject the combination material to determine a liquid volume of distribution and a liquid convection gradient within the liquid volume of distribution;
executing instructions with a processor to determine a therapy infusion parameter for infusion of the selected material to achieve a volume of efficacy in the subject of the selected material based on at least two of a study infusion parameter, the predetermined correlations of parameters, or the analyzed Peclet number; and
outputting the determined therapy infusion parameter.

12. The method of claim 11, further comprising:
generating the database by:
infusing the combination material into a subject model with at least one test infusion parameter;
comparing a test selected material volume of distribution and concentration gradient with a test liquid material volume of distribution and convection gradient;
determining a test correlation of (i) the test selected material volume of distribution and concentration gradient and (ii) the test liquid material volume of distribution and convection gradient; and
saving the test correlation in a memory device as the database.

13. The method of claim 12, wherein executing instructions with a processor to determine a therapy infusion parameter for infusion of the selected material includes calculating the therapy infusion parameter based on the determined test correlation.

14. The method of claim 12, wherein the test infusion parameter and the therapy infusion parameter are identical.

15. The method of claim 12, wherein the test infusion parameter and the therapy infusion parameter each include a plurality of infusion parameters.

16. The method of claim 12, wherein the test infusion parameter and the therapy infusion parameter each include at least one of a catheter location, a high flow rate, a low flow rate, a time at high flow rate, a time at low flow rate, a proxy material concentration, or a selected material concentration.

17. The method of claim 11, wherein executing instructions with the processor to determine the therapy infusion parameter for infusion of the selected material to achieve the volume of efficacy in the subject of the selected material based on the study infusion parameter, the predetermined correlations of parameters, and the analyzed Peclet number.

18. A system for determining a selected set of parameters for a therapy on a subject, comprising:
   a memory system configured to store a database of predetermined correlations of parameters relating a liquid material to a selected material, both of which are operable to be provided to the subject during the therapy;
   a processor configured to execute instructions to:
      analyze a Peclet number from T2 weighted magnetic resonance image data of the subject after having infused in the subject the liquid material to determine a liquid volume of distribution and a liquid convection gradient within the liquid volume of distribution,
      access the memory system to recall at least one correlation between the liquid material and the selected material from the database of predetermined correlations, and
      determine a therapy infusion parameter for infusion of the selected material to achieve a volume of efficacy in the subject of the selected material based on at least two of a test infusion parameter, the analyzed Peclet number, or the recalled at least one correlation; and
   a display device configured to display the determined therapy infusion parameter.

19. The system of claim 18, further comprising:
   a catheter configured to infuse at least one of the liquid material and the selected material; and
   a surgical navigation system configured to determine a location of the catheter during the infusion;
   wherein the infusion parameter includes the location of the catheter during the infusion.

20. The system of claim 18, further comprising:
   a catheter configured to infuse the selected material; and
   a surgical navigation system configured to determine when the catheter is at a determined infusion location of the catheter for infusion of the selected material;
   wherein the therapy infusion parameter includes the determined infusion location.

21. The system of claim 18, wherein the processor configured to execute instructions to determine the therapy infusion parameter for infusion of the selected material to achieve the volume of efficacy in the subject of the selected material is based on the test infusion parameter, the analyzed Peclet number, and the recalled at least one correlation.

* * * * *